United States Patent
Greenwood et al.

(10) Patent No.: US 12,396,730 B2
(45) Date of Patent: Aug. 26, 2025

(54) BRAIDED IMPLANT WITH DETACHMENT MECHANISM

(71) Applicant: DePuy Synthes Products, Inc., Raynham, MA (US)

(72) Inventors: Megan Greenwood, Raynham, MA (US); Scott Sloss, Raynham, MA (US); Tushar Sharma, Raynham, MA (US); William Cohn, Raynham, MA (US); Nicolo Garbin, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 462 days.

(21) Appl. No.: 17/954,458

(22) Filed: Sep. 28, 2022

(65) Prior Publication Data
US 2024/0099720 A1   Mar. 28, 2024

(51) Int. Cl.
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12168* (2013.01); *A61B 2017/00915* (2013.01); *A61B 2017/12054* (2013.01)

(58) Field of Classification Search
CPC ........ A61B 17/12113; A61B 17/12031; A61B 17/12168; A61B 17/17172; A61B 2017/00915; A61B 2017/12054; A61B 2017/00526
See application file for complete search history.

(56) References Cited

U.S. PATENT DOCUMENTS

| | | | |
|---|---|---|---|
| 3,429,408 | A | 2/1969 | Maker et al. |
| 5,108,407 | A | 4/1992 | Geremia et al. |
| 5,122,136 | A | 6/1992 | Guglielmi et al. |
| 5,217,484 | A | 6/1993 | Marks |

(Continued)

FOREIGN PATENT DOCUMENTS

| | | |
|---|---|---|
| EP | 1728478 A1 | 12/2006 |
| EP | 1985244 A2 | 10/2008 |

(Continued)

OTHER PUBLICATIONS

Extended European Search Report for European Application No. 20196478.0, mailed Jan. 25, 2021, 11 Pages.

(Continued)

*Primary Examiner* — Ryan J. Severson
(74) *Attorney, Agent, or Firm* — TROUTMAN PEPPER LOCKE LLP

(57) ABSTRACT

An occlusive device can include a segment including an open end and a proximal end. The occlusive device can include a push wire that is positioned proximal of the proximal end. The occlusive device can include a detachment feature that is attached to the push wire via a detachment groove. The occlusive device can include a sleeve surrounding the push wire. In a non-deployed configuration, the sleeve can surround the detachment feature and prevent release of the proximal end of the segment from the push wire. In a deployed configuration, the proximal end can be flush with a proximal end of the spherical cavity.

20 Claims, 7 Drawing Sheets

(56) References Cited

U.S. PATENT DOCUMENTS

| | | | |
|---|---|---|---|
| 5,250,071 A * | 10/1993 | Palermo | G02B 26/0825 |
| | | | 606/198 |
| 5,263,964 A | 11/1993 | Purdy | |
| 5,334,210 A * | 8/1994 | Gianturco | A61B 17/12222 |
| | | | 606/151 |
| 5,350,397 A | 9/1994 | Palermo et al. | |
| 5,382,259 A | 1/1995 | Phelps et al. | |
| 5,417,708 A * | 5/1995 | Hall | A61B 17/1215 |
| | | | 128/899 |
| 5,484,409 A | 1/1996 | Atkinson et al. | |
| 5,569,221 A | 10/1996 | Houser et al. | |
| 5,582,619 A | 12/1996 | Ken | |
| 5,624,449 A * | 4/1997 | Pham | A61B 17/12022 |
| | | | 606/1 |
| 5,853,418 A * | 12/1998 | Ken | A61B 17/12113 |
| | | | 606/198 |
| 5,899,935 A | 5/1999 | Ding | |
| 5,925,059 A | 7/1999 | Palermo et al. | |
| 6,113,622 A | 9/2000 | Tieshima | |
| 6,203,547 B1 | 3/2001 | Nguyen et al. | |
| 6,334,864 B1 * | 1/2002 | Amplatz | A61B 17/12172 |
| | | | 606/200 |
| 6,368,338 B1 * | 4/2002 | Konya | A61B 17/12109 |
| | | | 606/200 |
| 6,391,037 B1 | 5/2002 | Greenhalgh | |
| 6,454,780 B1 | 9/2002 | Wallace | |
| 6,506,204 B2 | 1/2003 | Mazzocchi | |
| 6,561,988 B1 | 5/2003 | Turturro et al. | |
| 6,636,758 B2 * | 10/2003 | Sanchez | A61B 90/39 |
| | | | 600/585 |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,708,754 B2 | 5/2010 | Balgobin et al. | |
| 7,708,755 B2 | 5/2010 | Davis, III et al. | |
| 7,722,636 B2 * | 5/2010 | Farnan | A61B 17/12022 |
| | | | 606/200 |
| 7,799,052 B2 | 9/2010 | Balgobin et al. | |
| 7,811,305 B2 | 10/2010 | Balgobin et al. | |
| 7,819,891 B2 | 10/2010 | Balgobin et al. | |
| 7,819,892 B2 | 10/2010 | Balgobin et al. | |
| 7,901,444 B2 | 3/2011 | Slazas | |
| 7,942,894 B2 | 5/2011 | West | |
| 7,985,238 B2 * | 7/2011 | Balgobin | A61M 29/00 |
| | | | 606/191 |
| 8,062,325 B2 | 11/2011 | Mitelberg et al. | |
| 8,333,796 B2 * | 12/2012 | Tompkins | A61B 17/12113 |
| | | | 623/1.11 |
| 8,449,591 B2 | 5/2013 | Litzenberg et al. | |
| 8,795,316 B2 * | 8/2014 | Balgobin | A61B 17/1214 |
| | | | 606/200 |
| 8,974,488 B2 | 3/2015 | Tan et al. | |
| 9,155,540 B2 * | 10/2015 | Lorenzo | A61B 17/1214 |
| 9,232,992 B2 | 1/2016 | Heidner | |
| 9,314,326 B2 | 4/2016 | Wallace et al. | |
| 9,486,223 B2 * | 11/2016 | Que | A61B 17/12145 |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,120 B2 | 5/2017 | Lagodzki et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 * | 7/2017 | Lam | A61F 2/0105 |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li | |
| 9,775,621 B2 | 10/2017 | Tompkins et al. | |
| 9,775,706 B2 * | 10/2017 | Peterson | A61F 2/966 |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,907,555 B2 * | 3/2018 | Buiser | A61B 17/12022 |
| 9,918,718 B2 | 3/2018 | Lorenzo | |
| 10,034,670 B2 | 7/2018 | Elgård et al. | |
| 10,282,851 B2 | 5/2019 | Gorochow | |
| 10,285,710 B2 | 5/2019 | Lorenzo et al. | |
| 10,517,604 B2 | 12/2019 | Bowman et al. | |
| 10,653,425 B1 | 5/2020 | Gorochow et al. | |
| 10,806,402 B2 | 10/2020 | Cadieu et al. | |
| 10,806,461 B2 | 10/2020 | Lorenzo | |
| 10,806,462 B2 | 10/2020 | Lorenzo | |
| 10,888,331 B2 | 1/2021 | Pederson et al. | |
| 11,051,928 B2 | 7/2021 | Casey et al. | |
| 2001/0049519 A1 | 12/2001 | Holman et al. | |
| 2001/0056281 A1 * | 12/2001 | Wallace | A61B 17/1214 |
| | | | 606/108 |
| 2002/0072705 A1 | 6/2002 | Vrba et al. | |
| 2002/0165569 A1 | 11/2002 | Ramzipoor et al. | |
| 2003/0216757 A1 * | 11/2003 | Gerberding | A61B 17/12172 |
| | | | 606/151 |
| 2004/0002731 A1 | 1/2004 | Aganon et al. | |
| 2004/0034363 A1 | 2/2004 | Wilson et al. | |
| 2004/0059367 A1 | 3/2004 | Davis et al. | |
| 2004/0087964 A1 | 5/2004 | Diaz et al. | |
| 2005/0149108 A1 * | 7/2005 | Cox | A61B 17/12022 |
| | | | 606/200 |
| 2006/0025802 A1 | 2/2006 | Sowers | |
| 2006/0064151 A1 | 3/2006 | Guterman | |
| 2006/0111771 A1 * | 5/2006 | Ton | A61F 2/962 |
| | | | 623/1.15 |
| 2006/0116711 A1 | 6/2006 | Elliott et al. | |
| 2006/0135021 A1 | 6/2006 | Calhoun et al. | |
| 2006/0155303 A1 * | 7/2006 | Konya | A61B 17/12122 |
| | | | 606/108 |
| 2006/0276824 A1 | 12/2006 | Mitelberg et al. | |
| 2006/0276825 A1 | 12/2006 | Mitelberg et al. | |
| 2006/0276826 A1 | 12/2006 | Mitelberg et al. | |
| 2006/0276827 A1 | 12/2006 | Mitelberg et al. | |
| 2006/0276830 A1 | 12/2006 | Balgobin et al. | |
| 2006/0276833 A1 | 12/2006 | Balgobin et al. | |
| 2007/0010850 A1 | 1/2007 | Balgobin et al. | |
| 2007/0083132 A1 | 4/2007 | Sharrow | |

(56) References Cited

U.S. PATENT DOCUMENTS

| | | | |
|---|---|---|---|
| 2007/0083226 A1* | 4/2007 | Buiser | A61B 17/12113 606/200 |
| 2007/0179520 A1* | 8/2007 | West | A61B 17/1214 606/200 |
| 2007/0203519 A1* | 8/2007 | Lorenzo | A61B 17/1214 606/200 |
| 2007/0233168 A1 | 10/2007 | Davis et al. | |
| 2007/0270903 A1 | 11/2007 | Davis, III et al. | |
| 2007/0270930 A1 | 11/2007 | Schenck | |
| 2007/0299422 A1* | 12/2007 | Inganas | A61B 17/1214 606/191 |
| 2008/0027561 A1 | 1/2008 | Mitelberg et al. | |
| 2008/0035160 A1 | 2/2008 | Woodson et al. | |
| 2008/0045997 A1 | 2/2008 | Balgobin et al. | |
| 2008/0082113 A1 | 4/2008 | Bishop et al. | |
| 2008/0097462 A1 | 4/2008 | Mitelberg et al. | |
| 2008/0119887 A1 | 5/2008 | Que et al. | |
| 2008/0221654 A1* | 9/2008 | Buiser | A61B 17/12145 606/191 |
| 2008/0281350 A1 | 11/2008 | Sepetka | |
| 2008/0300616 A1 | 12/2008 | Que et al. | |
| 2008/0306503 A1 | 12/2008 | Que et al. | |
| 2009/0036877 A1* | 2/2009 | Nardone | A61B 17/12022 606/1 |
| 2009/0062726 A1 | 3/2009 | Ford et al. | |
| 2009/0099592 A1 | 4/2009 | Buiser et al. | |
| 2009/0177261 A1* | 7/2009 | Teoh | A61B 17/12022 623/1.11 |
| 2009/0312748 A1 | 12/2009 | Johnson et al. | |
| 2010/0094395 A1* | 4/2010 | Kellett | A61B 17/1215 623/1.11 |
| 2010/0114017 A1 | 5/2010 | Lenker et al. | |
| 2010/0160944 A1 | 6/2010 | Teoh et al. | |
| 2010/0324649 A1 | 12/2010 | Mattsson | |
| 2011/0092997 A1 | 4/2011 | Kang | |
| 2011/0295303 A1 | 12/2011 | Freudenthal | |
| 2012/0035707 A1 | 2/2012 | Mitelberg et al. | |
| 2012/0041472 A1 | 2/2012 | Tan et al. | |
| 2012/0283768 A1 | 11/2012 | Cox et al. | |
| 2013/0066413 A1 | 3/2013 | Jin et al. | |
| 2013/0138136 A1* | 5/2013 | Beckham | A61B 17/12136 29/520 |
| 2013/0338701 A1 | 12/2013 | Wilson et al. | |
| 2014/0058435 A1* | 2/2014 | Jones | A61B 17/1214 606/200 |
| 2014/0135812 A1 | 5/2014 | Divino et al. | |
| 2014/0200607 A1 | 7/2014 | Sepetka et al. | |
| 2014/0207175 A1 | 7/2014 | Aggerholm | |
| 2014/0277085 A1 | 9/2014 | Mirigian et al. | |
| 2014/0277092 A1 | 9/2014 | Teoh et al. | |
| 2014/0277093 A1 | 9/2014 | Guo et al. | |
| 2015/0112378 A1* | 4/2015 | Torp | A61B 17/1214 606/1 |
| 2015/0182227 A1 | 7/2015 | Le et al. | |
| 2015/0230802 A1 | 8/2015 | Lagodzki et al. | |
| 2015/0335333 A1 | 11/2015 | Jones et al. | |
| 2016/0022275 A1 | 1/2016 | Garza | |
| 2016/0157869 A1 | 6/2016 | Elgård et al. | |
| 2016/0228125 A1 | 8/2016 | Pederson, Jr. et al. | |
| 2016/0310304 A1 | 10/2016 | Mialhe | |
| 2016/0346508 A1 | 12/2016 | Williams et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1* | 3/2017 | Pung | A61F 2/82 |
| 2017/0079820 A1* | 3/2017 | Lam | A61F 2/966 |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |
| 2017/0105739 A1 | 4/2017 | Dias et al. | |
| 2017/0113023 A1 | 4/2017 | Steingisser et al. | |
| 2017/0135801 A1* | 5/2017 | Delaney, Jr. | A61B 17/12122 |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1* | 6/2017 | Vong | A61F 2/885 |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0245864 A1 | 8/2017 | Franano et al. | |
| 2017/0245885 A1 | 8/2017 | Lenker | |
| 2017/0252064 A1 | 9/2017 | Staunton | |
| 2017/0258476 A1 | 9/2017 | Hayakawa et al. | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1* | 10/2017 | Corwin | A61F 2/07 |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2018/0028779 A1 | 2/2018 | von Oepen et al. | |
| 2018/0228493 A1* | 8/2018 | Aguilar | A61B 17/12113 |
| 2018/0250150 A1 | 9/2018 | Majercak et al. | |
| 2018/0280667 A1 | 10/2018 | Keren | |
| 2018/0289375 A1 | 10/2018 | Hebert et al. | |
| 2018/0325706 A1 | 11/2018 | Hebert et al. | |
| 2019/0192162 A1 | 6/2019 | Lorenzo et al. | |
| 2019/0255290 A1 | 8/2019 | Snyder et al. | |
| 2019/0328398 A1 | 10/2019 | Lorenzo | |
| 2020/0093499 A1* | 3/2020 | Lorenzo | A61B 17/12172 |

(56) References Cited

U.S. PATENT DOCUMENTS

2020/0229957 A1    7/2020   Bardsley et al.
2021/0001082 A1    1/2021   Lorenzo et al.

FOREIGN PATENT DOCUMENTS

| EP | 3092956 A1 | 11/2016 |
|----|------------|---------|
| EP | 3501427 A1 | 6/2019 |
| EP | 3760139 A2 | 1/2021 |
| JP | 2006-334408 A | 12/2006 |
| JP | 2012-000464 A | 1/2012 |
| JP | 2012-523943 A | 10/2012 |
| JP | 2013-78584 A | 5/2013 |
| JP | 2013-212372 A | 10/2013 |
| WO | WO 2012/158152 A1 | 11/2012 |

OTHER PUBLICATIONS

Extended European Search Report for European Application No. 22184571.2, mailed Dec. 8, 2022, 8 pages.
Extended European Search Report for European Application No. 22184574.6, mailed Dec. 6, 2022, 10 pages.

\* cited by examiner

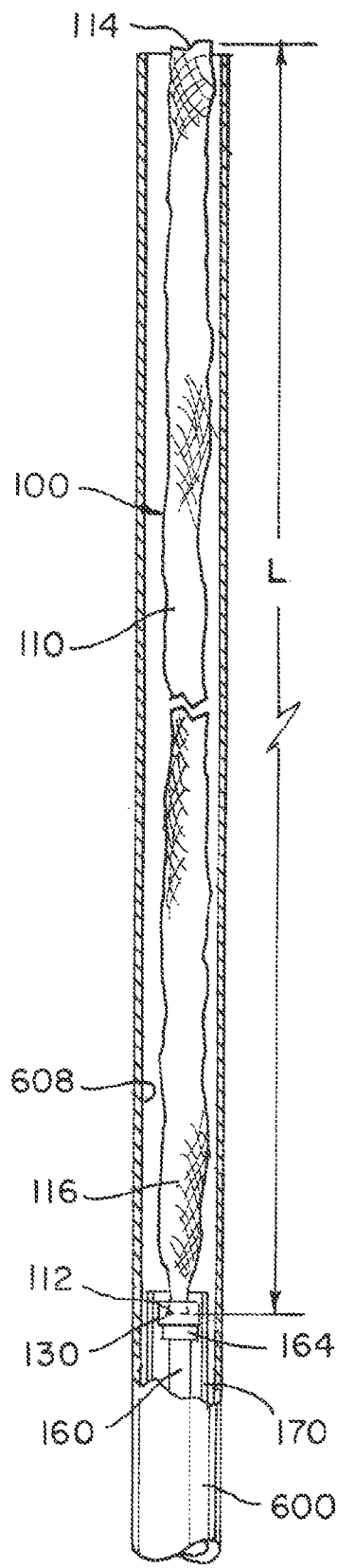
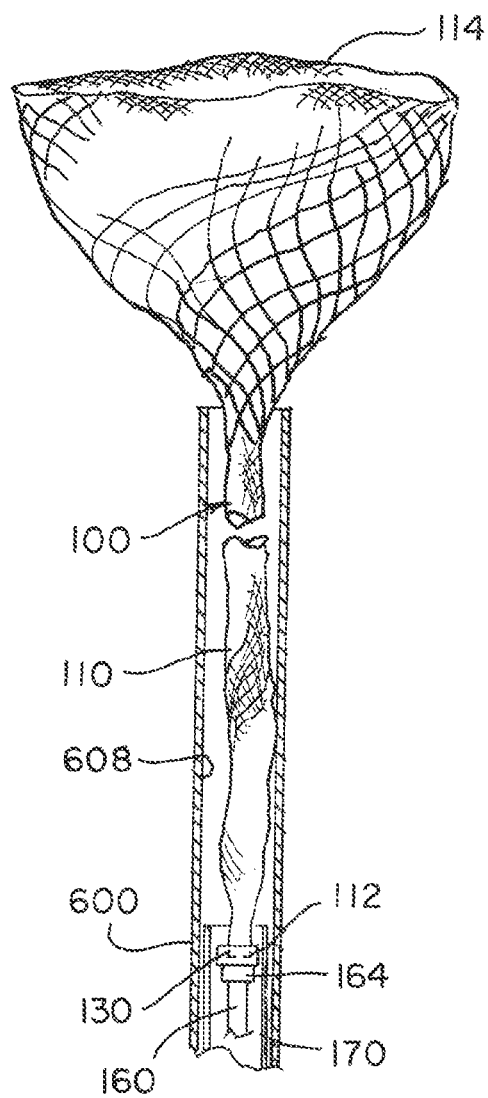

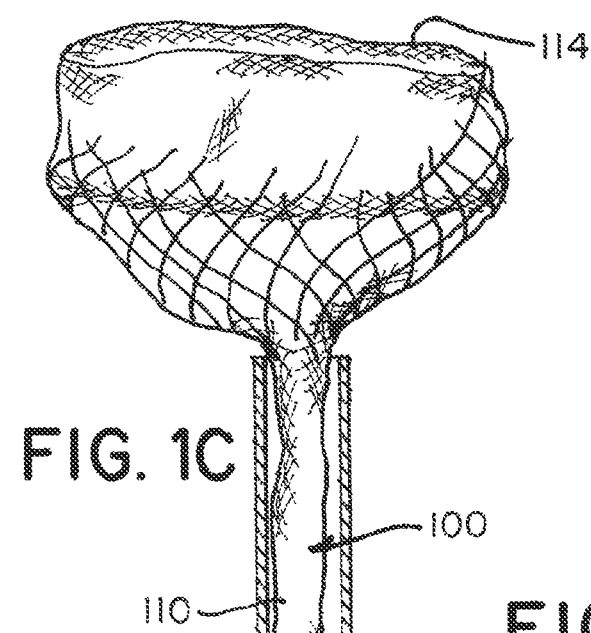
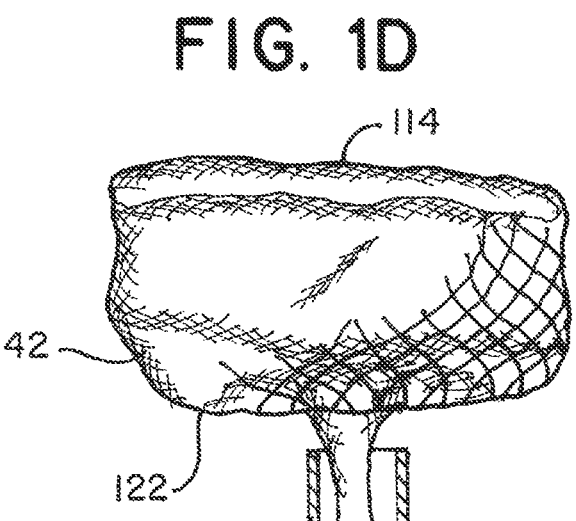
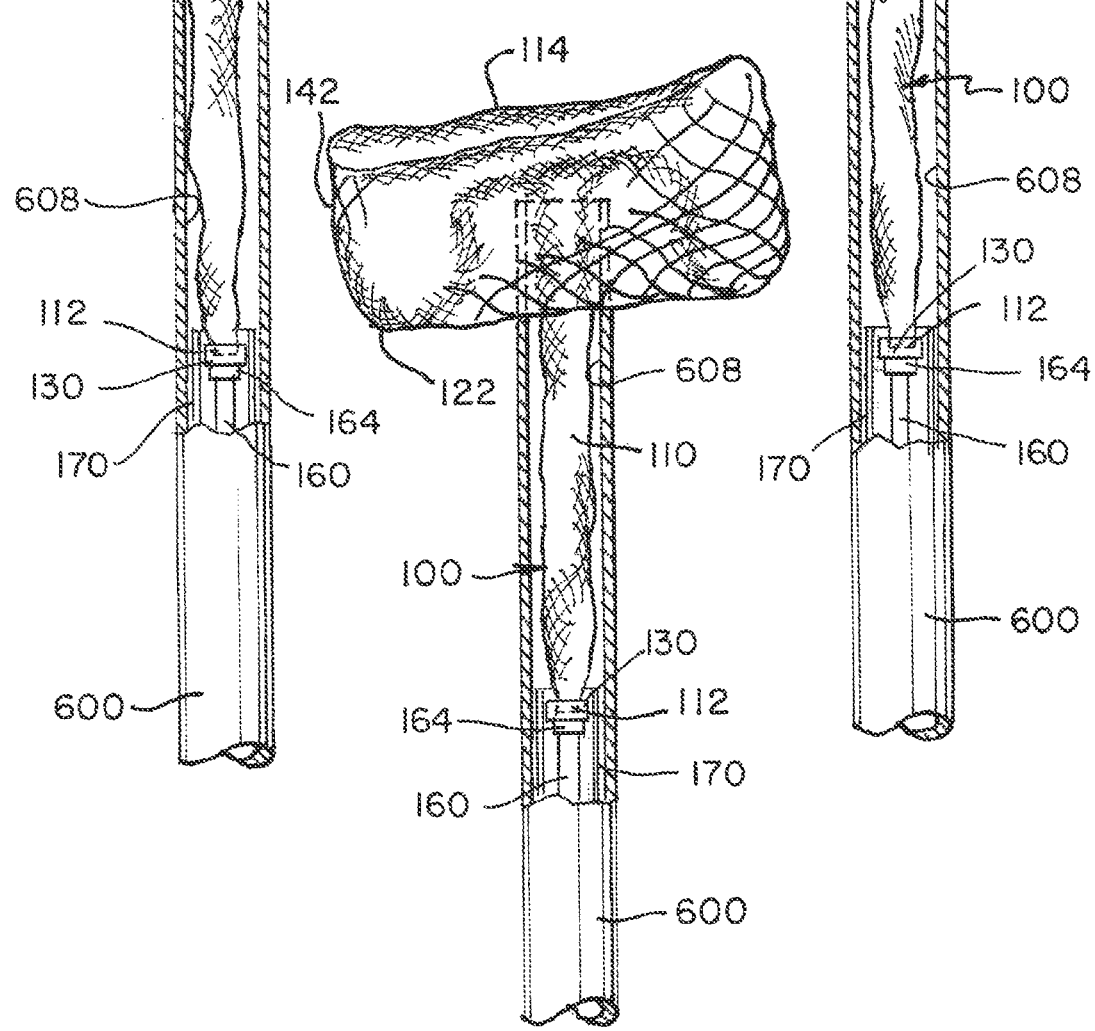

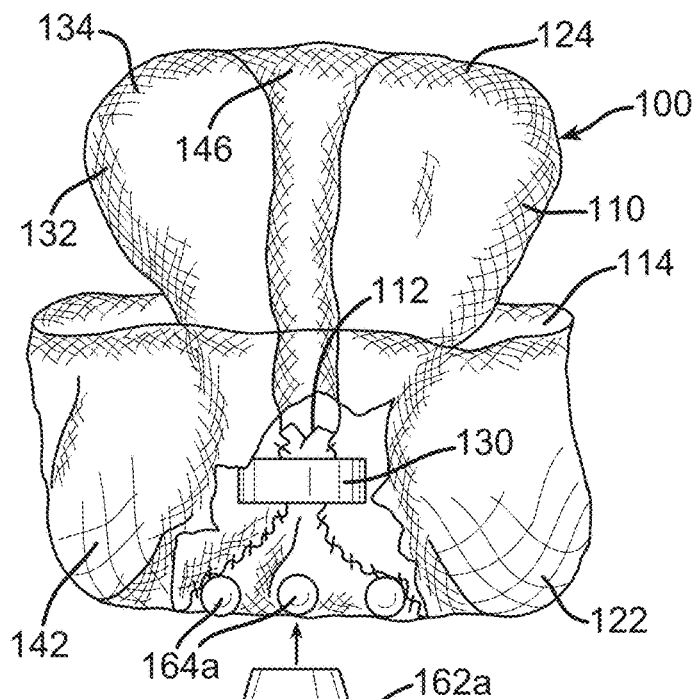
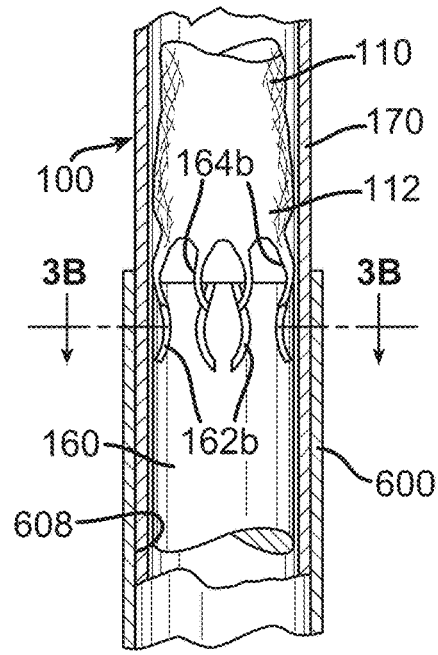
FIG. 3A
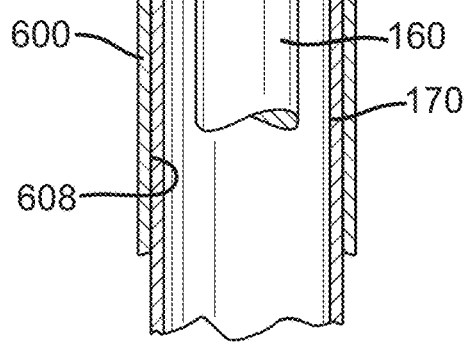
FIG. 2C
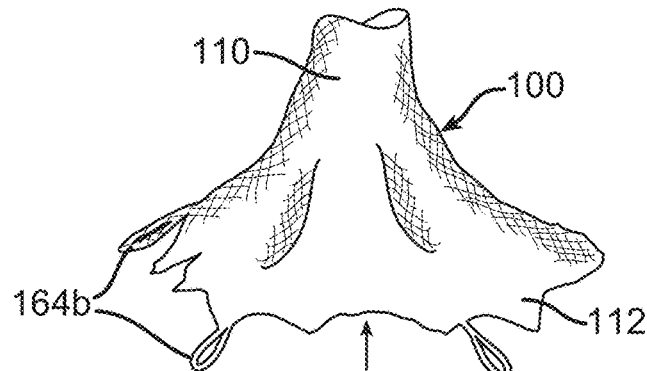
FIG. 3C
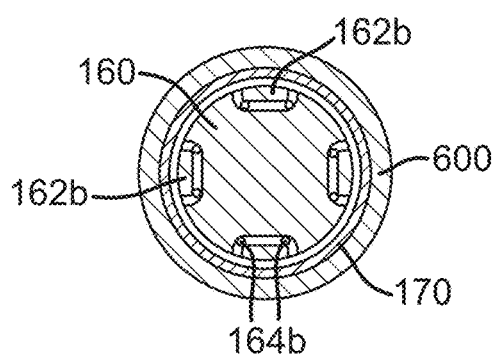
FIG. 3B
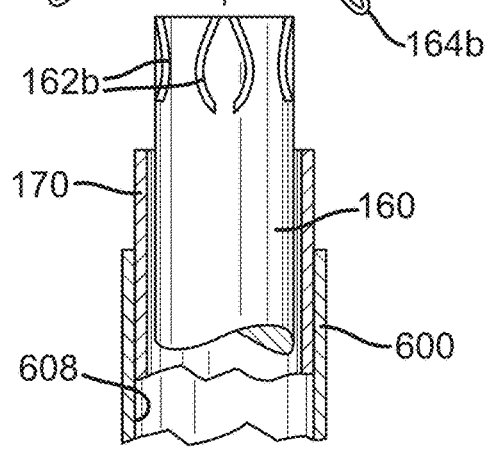

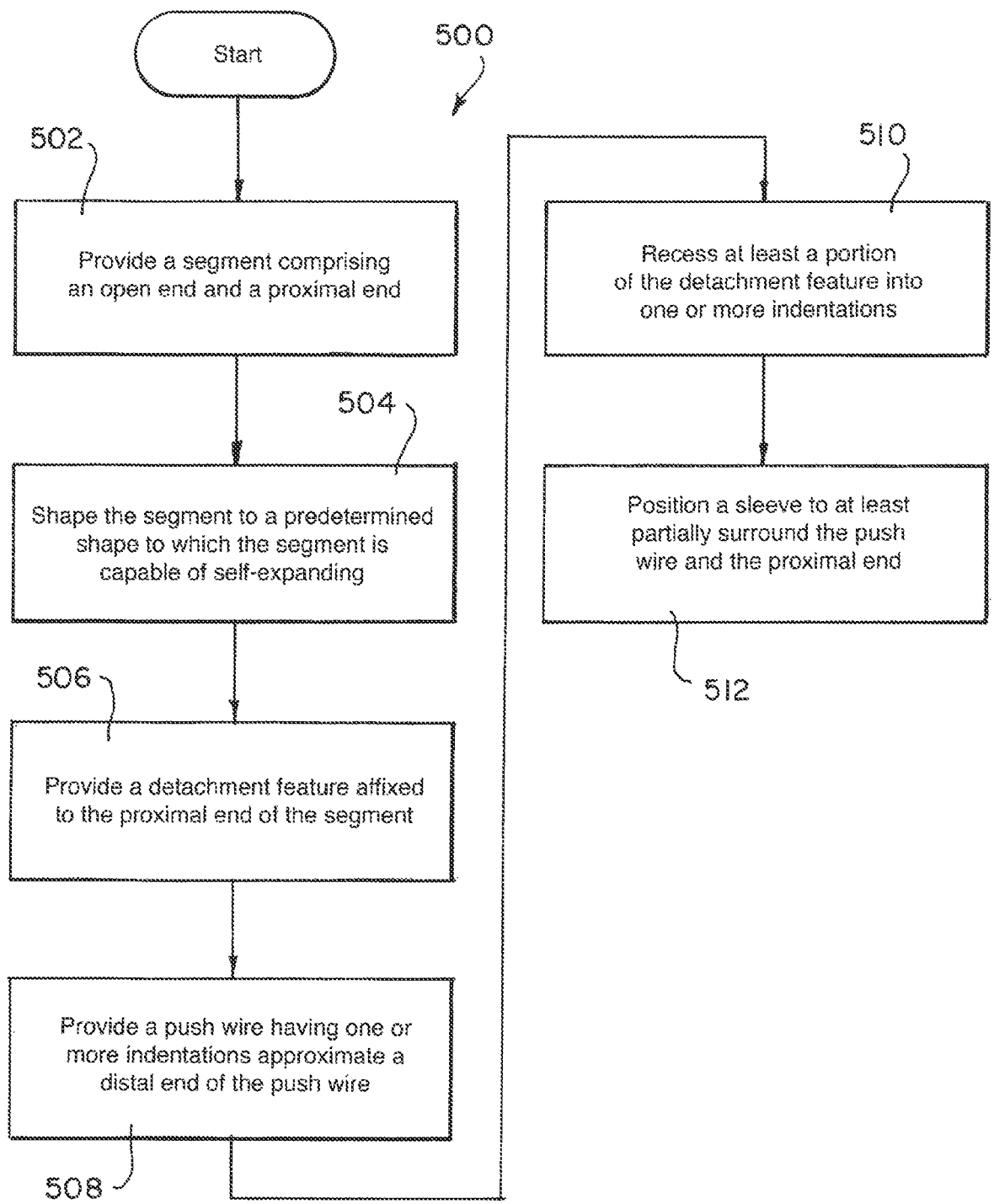

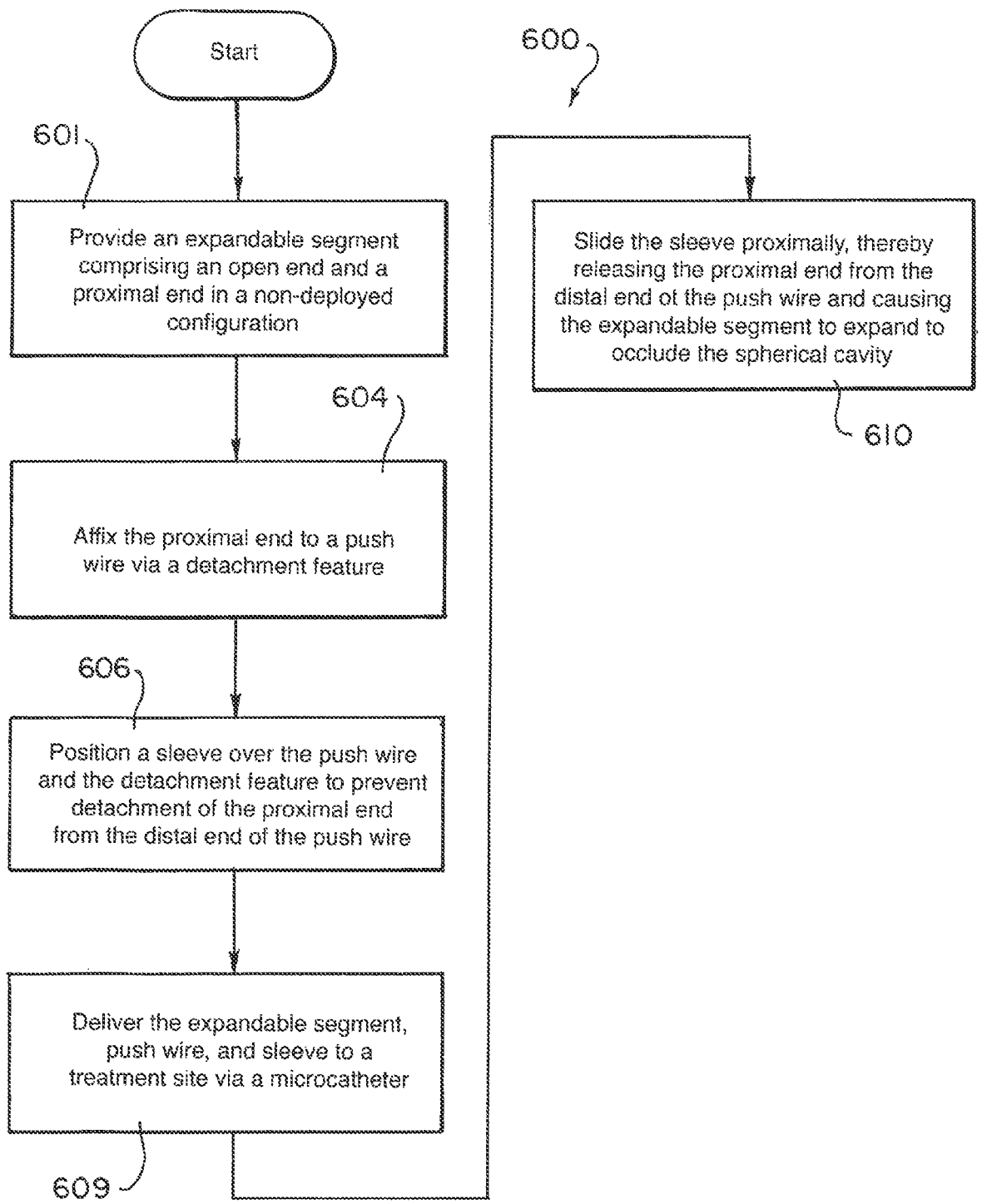

BRAIDED IMPLANT WITH DETACHMENT MECHANISM

FIELD OF INVENTION

The present invention generally relates to medical instruments, and more particularly, to embolic implants detachment mechanisms for aneurysm therapy.

BACKGROUND

Cranial aneurysms can be complicated and difficult to treat due to their proximity to critical brain tissues. Recently, tubular braided implants have been introduced that have the potential to treat an aneurysm or other arterio-venous malformation easily, accurately, and safely in a parent vessel without blocking flow into perforator vessels communicating with the parent vessel. Implant devices for treating aneurysms must be delivered through long, small, tortuous blood vessels and positioning must be controlled precisely to ensure aneurysm filling without causing additional occlusions or clotting in nearby vessels. Accordingly, it is necessary to have a delivery and detachment mechanism providing the connection point between a tubular braided implant and a delivery catheter that has the ability to deliver, position, manipulate, and then release the implant.

SUMMARY

It is an object of the present invention to provide systems, devices, and methods to meet the above-stated needs. Generally, it is an object of the present invention to provide an endovascular implantation system for occluding a spherical cavity. The endovascular implantation system can include an occlusive segment that includes an open end and a proximal end and is configured to occlude a spherical cavity. The endovascular implantation system can include a push wire that is positioned proximal of the proximal end of the occlusive segment. The push wire can include one or more indentations on an outer surface of the push wire approximate a distal end of the push wire. The proximal end of the occlusive segment can include a detachment feature that is shaped to at least partially recess into the one or more indentations of the push wire. The occlusive device can include a sleeve surrounding at least a portion of the push wire. In a non-deployed configuration, the sleeve can at least partially surround the detachment feature and prevent release of the proximal end of the occlusive segment from the push wire. In a deployed configuration, the sleeve can be retracted proximally from the detachment feature to thereby detach the occlusive segment from the push wire.

In some examples, the detachment feature can further include a plurality of wire loops that extend from the proximal end of the segment that are configured to fit into the one or more indentations that are positioned on a distal tip of the push wire.

In some examples, the one or more indentations can include a plurality of laser-etched pockets. Each of the laser-etched pockets can be shaped to fit a corresponding wire loop of the plurality of wire loops.

In some examples, the detachment feature can further include a plurality of balls that extend from the proximal end of the segment. The plurality of balls can be configured to fit into the one or more indentations positioned on distal tip of the push wire.

In some examples, the one or more indentations can include an annular groove circumscribing an outer surface of the push wire.

In some examples, in the deployed configuration, the occlusive segment can expand to occlude the spherical cavity.

In some examples, in the deployed configuration the occlusive segment can extend in a distal direction from the proximal end and can include two inversions that separate three sections of the segment which at least partially overlap each other such that the proximal end is affixed to an innermost section of the three sections and a middle section of the three sections can extend between the two inversions and is positioned within an outermost section and around the innermost section.

In some examples, the endovascular implantation system can include a microcatheter that is configured to deliver the occlusive segment, the push wire, and the sleeve to the spherical cavity with the occlusive device in the non-deployed configuration. The microcatheter can include a lumen, and the segment can have a diameter in the non-deployed configuration sized to fit within the lumen of the microcatheter.

In some examples, the endovascular implantation system can include a band that is approximate the proximal end of the segment. The band can include radiopaque material.

In some examples, in the deployed configuration, the open end of the occlusive segment can be positioned approximate a distal wall of the spherical cavity and the band can be suspended within the spherical cavity.

In some examples, the spherical cavity can be an aneurysm sac.

In some examples, the occlusive segment can include a tubular braid.

In another aspect, a method for constructing an endovascular treatment system is disclosed. The method can include providing an occlusive segment that includes an open end and a proximal end. The method can include shaping the occlusive segment to a predetermined shape to which the segment is capable of self-expanding. Shaping the predetermined shape can include inverting the segment to form a proximal inversion that is folded towards the distal direction to thereby define an outermost section of the segment. Shaping the predetermined shape can include inverting the segment to form a distal inversion folded toward the proximal direction to thereby define a middle section between the proximal and distal inversion of the segment that is at least partially surrounded by the outermost section and defines an innermost section between the distal inversion and the proximal end that is at least partially surrounded by the middle section. The method can include providing a detachment feature that is affixed to the proximal end of the segment. The method can include providing a push wire having one or more indentations in a distal end of the push wire. The method can include recessing at least a portion of the detachment feature into the one or more indentations of the push wire. The method can include positioning a sleeve to at least partially surround the push wire and the detachment feature.

In some examples, the sleeve is effective to retain the proximal end of the segment attached to the push wire.

In some examples, the detachment feature can further include a plurality of wire loops that extend from the proximal end that can be configured to fit into the one or more indentations positioned on the distal end of the push wire.

In some examples, the one or more indentations can include a plurality of laser-etched pockets. Each of the laser-etched pockets can be shaped to fit a corresponding wire loop of the plurality of wire loops.

In some examples, the detachment feature can further include a plurality of balls that extend from the proximal end of the segment. The plurality of balls can be configured to fit into the one or more indentations that are positioned on the distal end of the push wire.

In some examples, in the deployed configuration, the proximal end of the segment can be flush with a proximal end of the spherical cavity. In some examples, the spherical cavity can be an aneurysm sac.

In another aspect, a method of occluding a spherical cavity is disclosed. The method can include providing an expandable segment that includes an open end and a proximal end in a non-deployed configuration. The method can include affixing the proximal end to a push wire via a detachment feature. The method can include positioning a sleeve over at least a portion of the push wire and at least a portion of the detachment feature to prevent detachment of the proximal end of the expandable segment from the distal end of the push wire. The method can include delivering the expandable segment, push wire, and sleeve to a treatment site via a microcatheter. The method can include sliding the sleeve proximally, thereby releasing the proximal end from the distal end of the push wire and causing the expandable segment to expand to a deployed configuration to occlude the spherical cavity.

In some examples, the detachment feature can further include a plurality of wire loops that extend from the proximal end that can be configured to fit into the one or more indentations positioned on the distal end of the push wire.

In some examples, the one or more indentations can include a plurality of laser-etched pockets. Each of the laser-etched pockets can be shaped to fit a corresponding wire loop of the plurality of wire loops.

In some examples, the detachment feature can further include a plurality of balls that extend from the proximal end of the segment. The plurality of balls can be configured to fit into the one or more indentations that are positioned on the distal end of the push wire.

In some examples, the one or more indentations can include an annular groove circumscribing an outer surface of the push wire.

In some examples, the proximal end is flush with a proximal end of the spherical cavity. In some examples, the spherical cavity can be an aneurysm.

In some examples, in the deployed configuration, the expandable segment can include two inversions that separate three sections which at least partially overlap each other such that the proximal end is affixed to an innermost section of the three sections, and a middle section of the three sections extends between the two inversion and is positioned within an outermost section and around the innermost section.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 1A through 1G are illustrations of an example endovascular treatment system including an implant having a tubular braid that expands to a predetermined shape as the tubular braid exits a microcatheter according to aspects of the present invention;

FIG. 2C is an illustration of the system of FIG. 2A with the detachment feature in a deployed configuration, according to aspects of the present invention;

FIG. 3A is an illustration of another example endovascular treatment system including an implant with a detachment feature including loops and a push wire including laser-etched pockets in a non-deployed configuration, according to aspects of the present invention;

FIG. 3B is a cross-sectional illustration of the system of FIG. 3A according to aspects of the present invention;

FIG. 3C is an illustration of the system of FIG. 3A with the detachment feature in a deployed configuration, according to aspects of the present invention;

FIG. 5 is a flowchart of a method for constructing an endovascular treatment system, according to aspects of the present invention; and FIG. 6 is a flowchart of a method for occluding a spherical cavity, according to aspects of the present invention.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Examples presented herein generally include a braided implant that can secure within an aneurysm sac and occlude a majority of the aneurysm's neck. The implant can include a tubular braid that can be set into a predetermined shape, compressed for delivery through a microcatheter, and implanted in at least one implanted position that is based on the predetermined shape and the geometry of the aneurysm in which the braid is implanted. When compressed, the implant can be sufficiently short to mitigate friction forces produced when the implant is delivered unsheathed through the microcatheter allowing for a more simplistic delivery system compared to some other known braided embolic implant delivery systems. The implant can be as described in U.S. Pat. No. 10,653,425, the entirety of which is incorporated herein by reference as if included in full.

Figure 1F:
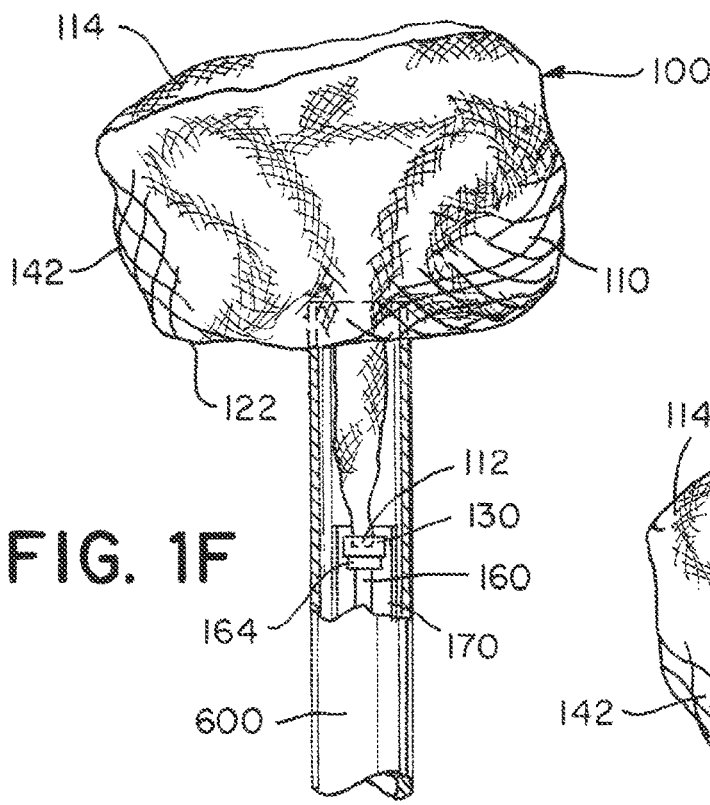

FIGS. 1A through 1G are illustrations of an example implant 100 having a segment 110 expanding to a deployed configuration as the segment 110 exits a microcatheter 600. The implant 100 can have a deployed shape similar to as illustrated below in reference to FIGS. 1G, 2C and 4B. As illustrated in FIG. 1A, the segment 110 can be shaped to a non-deployed shape that is extended to a single layer of tubular braid having a compressed circumference/diameter sized to be delivered through the microcatheter 600 and a length L. The illustrated implant 100 can have a length L of between about 22 mm and about 25 mm. As will be appreciated and understood by a person skilled in the art, the length L of a specific segment 110 can be tailored based on the size and shape of the aneurysm being treated.

During delivery through the microcatheter 600, the detachment feature 164 can be attached to a delivery system at a proximal end 112 of the implant 100, and the open end 114 can define the distal end of the implant 100. The delivery system is drawn simplistically in FIGS. 1A through 1C for the sake of simplicity of illustration, and example delivery system configurations are shown in greater detail in FIGS. 2A through 2C and 3A through 3C. Collapsing the segment 110 to a single layer tube can result in a segment 110 that has a sufficiently small diameter and a sufficiently short length L to mitigate effects of friction force on the segment 110 when it is delivered through lumen 608 of the microcatheter 600, allowing the segment 110 to be delivered unsheathed in some applications. In some applications, segment 110 is delivered through lumen 608 of microcatheter 600 with a sheath 170 covering some or all of segment 110. Sheath 170 can be configured to be placed over at least detachment feature 164 to keep detachment feature 164 from releasing the connection between a distal end of push wire 160 and the implant 110.

As illustrated in FIG. 1B, the open end 114 can be positioned to exit the microcatheter 600 before any other portion of the segment 110 exits the microcatheter. The open end 114 can expand as it exits the microcatheter 600. If the open end 114 is unconstrained by an aneurysm as illustrated, the open end can expand to its circumference in the predetermined shape.

As illustrated in FIG. 1C, the distal portion of the segment 110 can continue to expand radially as it exits the microcatheter 600.

As illustrated in FIG. 1D, the segment 110 can form an inversion 122 defining an outer section 142 as the segment 110 is further pushed out of the microcatheter 600.

Figure 1G:
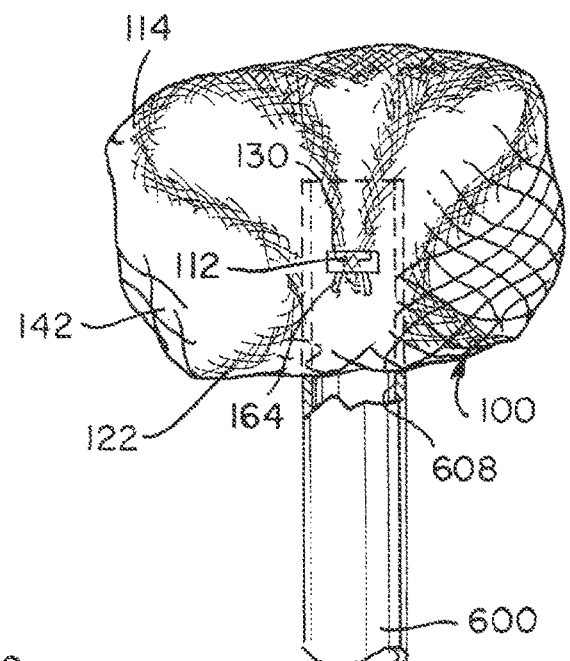

As illustrated in FIGS. 1E, 1F, and 1G, the "S" shape of a middle section 144 can begin to form as the segment 110 is further pushed from the microcatheter 600.

Figure 2A:
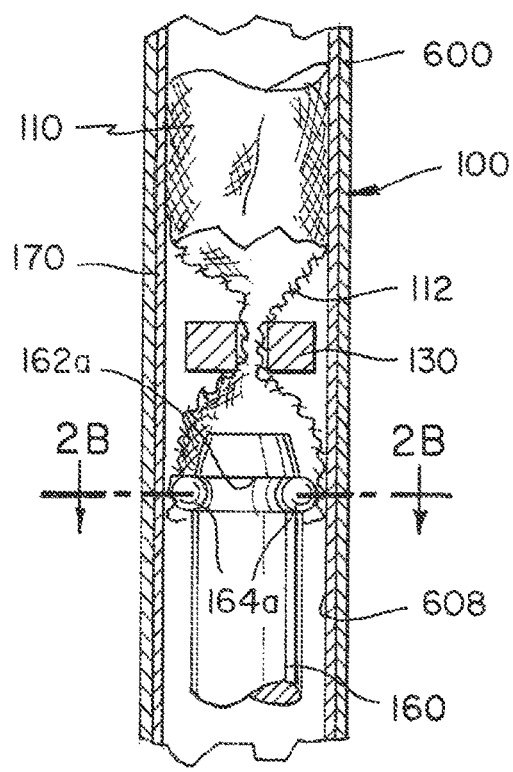
FIG. 2A is an illustration of an example endovascular treatment system including an implant with a detachment feature that includes balls in a non-deployed configuration, according to aspects of the present invention.
Figure 2B:
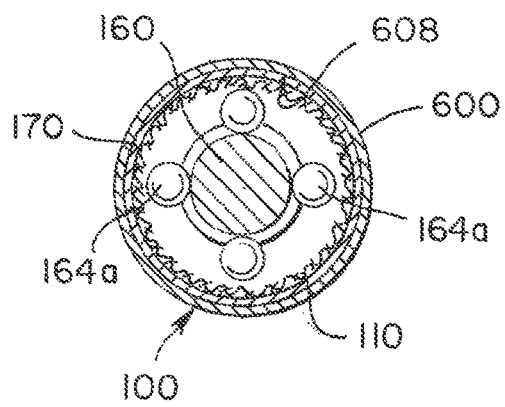
FIG. 2B is cross-sectional illustration of the system as indicated in FIG. 2A according to aspects of the present invention.

FIG. 2A is an illustration of an example endovascular treatment system 100 including an implant with a detachment feature, in a non-deployed configuration, that includes balls, according to an exemplary embodiment. FIG. 2B is cross-sectional illustration of the system 100 as indicated in FIG. 2A. As shown, implant 100 can be delivered through a lumen 608 of microcatheter 600 to a treatment site. The implant can include a segment 110 which can be formed as a heat-set tubular braided implant that, when released from the microcatheter at a treatment site, the segment 110 can expand into a deployed configuration as shown in FIG. 2C. The segment can include an open end 114 (not shown) and a proximal end 112 that can be attached to a push wire 160 via a detachment feature 164A. Detachment feature 164A can include one or more balls that are shaped to fit into one or more indentations 162A located on distal end of push wire 160. The one or more indentations 162 can include an annular groove circumscribing the outer surface of the push wire 160 that is sized to receive the balls. Additionally, or alternatively, the one or more indentations 162 can include a plurality of circular or semi-spherical pockets sized to receive the balls. A sheath 170 can be positioned over the implant 100 such that sheath 170 covers at least a portion of the detachment feature 164A, thereby retaining the detachment feature 164A at least partially recessed within the one or more indentations 162A until the sheath 170 is removed. As illustrated, approximate the proximal end of the segment 110 can be a band 130. However, band 130 is an optional feature and implant 100 can be configured to not include band 130. Band 130 can be made of a radiopaque material in order to facilitate tracking the position of implant 100 as implant 100 is delivered through vasculature to a treatment site.

FIG. 2C is an illustration of the system of FIG. 2A in a deployed configuration. After implant 100 is delivered to a treatment site (e.g., spherical cavity 10, as described below in FIG. 4A), the implant 100 can be manipulated to expand from the non-deployed configuration to the deployed configuration by pushing the implant 100 out from microcatheter 600. FIG. 2C shows the implant 100 detached from push wire 160. The sheath 170 has been removed by being slid proximally into microcatheter 600, thus allowing detachment feature 164A to detach from the one or more indentations 162A. In some examples, there can be one detachment feature 164A and one corresponding indentation or groove 162A, two detachment features 164A and two corresponding indentations or grooves 162A, or more than two detachment features 164A and corresponding indentations or grooves 162A. As shown, implant 100 can expand to the deployed configuration having two inversions 122, 124, dividing the segment 110 into three segments 142, 144, 146. In the deployed configuration, the segment 110 can have an outer section 142 extending from the open end 114 of the segment 110 to one of the inversions 122, an inner section 146 extending from the proximal end 112 of the segment 110 to the other of the inversions 124, and a middle section 144 extending between the two inversions 122, 124.

FIG. 3A is an illustration of another example endovascular treatment system including an implant with a detachment feature including loops and a push wire including laser-etched pockets in a non-deployed configuration. Proximal end 112 of implant 100 segment 110 is shown with sheath 170 extended over the proximal end 112 in FIG. 3A. Sheath 170 can be translated proximally, thereby exposing the proximal end 112 of segment 110 and allowing detachment feature 164B to be released from corresponding grooves 162B. The detachment feature 164B can be one or more loops formed on the proximal end 112 of the implant segment 110. Push wire 160 can include one or more indentations 162B on the distal end of push wire 160. In some examples, the one or more indentations 162B can include laser-etched pockets that are shaped to fit the one or more loops of detachment feature 164B.

FIG. 3B is a cross-sectional view of the system 100 showing the loop and pocket detachment mechanism as indicated in FIG. 3A. As can be seen in FIG. 3B, the pockets 162B can extend radially into the push wire 160 and correspond to the shape of the one or more loops of detachment feature 164B.

FIG. 3C is an illustration of the system 100 after the detachment feature 164b expands so that loops release from the indentations 162B of the push wire 160. The sheath 170 is retracted to allow the detachment feature 164b to expand.

Figure 4A:
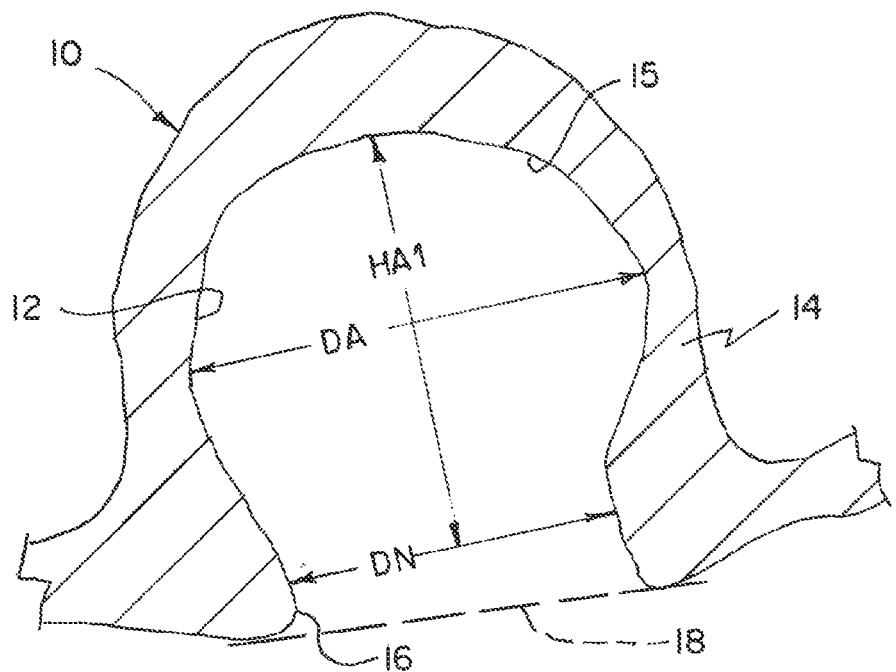
FIGS. 4A and 4B are illustrations of measurements of an example spherical cavity and implant according to aspects of the present invention.
Figure 4B:
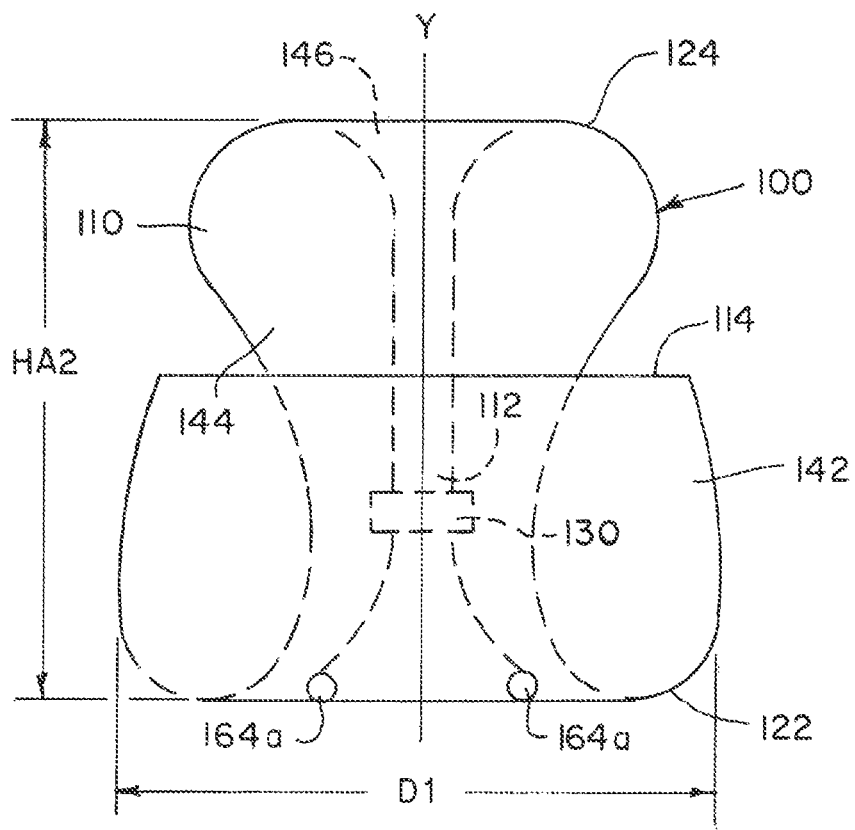

FIGS. 4A and 4B are illustrations of measurements of an example spherical cavity and implant according to aspects of the present invention. FIG. 4A is an illustration of height HA1 sac diameter DA, and neck diameter DN, which are measurements of a spherical cavity 10. In some examples, spherical cavity can be an aneurysm of a patient. The location of the plane 18 defining a boundary between the spherical cavity 10 and blood vessels is also illustrated. As shown, the spherical cavity 10 can include a neck 16, a wall 14, and a distal wall 15. The spherical cavity 10 can also include a spherical cavity interior 12. The endovascular implant 100 can be configured to occlude the spherical cavity 10 when the implant is in a deployed configuration.

FIG. 4B is an illustration of height HA2 of an example implant 100 in a deployed configuration. In the deployed configuration, the braid 110 of the example implant 100 can be substantially radially symmetrical about vertical axis y, and therefore can have substantially circular concentric cross-sections each describable by its diameter. FIG. 4B highlights the height HA2 of the implant 100 in a deployed configuration measured between the inversions 122, 124, an outer diameter D1 of the outer section 142, which corresponds to the diameter of the open end 114, and the outer diameter D2 of the middle section 144. It should be understood that the height HA2 of example implant 100 can be varied to match the height HA1 of spherical cavity 10 such that a proximal end of segment 110 is flush with a proximal end of the spherical cavity 10 in the deployed state. For example, the proximal end of segment 110 can be flush with the plane 18 when in the deployed configuration, as shown in FIG. 4A. Although FIG. 4B illustrates only one example deployed configuration, it should be understood that the height and diameter of example implants described herein 100 and portions thereof can be varied to fit spherical cavities 10 of varying dimensions.

FIG. 5 is a flowchart of a method 500 for constructing an endovascular treatment system. In block 502, the method can include providing a segment 110 including an open end 114 and a proximal end 112. The segment can include a braided tubular implant. The open end can be on a distal end of the segment.

In block 504, the method can include shaping the segment to a predetermined shape to which the segment is capable of self-expanding. Shaping the segment to a predetermined shape can include inverting the segment to form a proximal inversion 122 folded towards the distal direction thereby defining an outermost section 142 of the segment. Shaping the segment to a predetermined shape can include inverting the segment to form a distal inversion 124 folded toward the proximal direction to define a middle section 144 between the proximal and distal inversion of the segment. The middle section of the segment can be at least partially surrounded by the outermost section and define an innermost section 146 between the distal inversion and the proximal end 112 that is at least partially surrounded by the middle section 144.

In block 506, the method can include providing a detachment feature 164 that is affixed to the proximal end of the segment. In some examples, the detachment feature 164 can include one or more balls 164A that are configured to fit into one or more indentations 162A formed within a distal end of push wire 160. In some examples, the detachment feature 164 can include one or more wire loops 164B formed from a proximal end of the segment 110 of the implant 100, and the one or more wire loops 164B are configured to fit into the one or more indentations 162B formed within a distal end of push wire 160.

In block 508, the method can include providing a push wire 160 that includes one or more indentations 162 in a distal end of the push wire 160.

In block 510, the method can include recessing at least a portion of the detachment feature 164 into the one or more indentations on the push wire.

In block 512, the method can include positioning a sleeve 170 at least partially surrounding the push wire 160 and the proximal end 112 of the segment 110.

FIG. 6 is a flowchart of a method 601 for occluding a spherical cavity. In block 602, the method can include providing an expandable segment 110 that includes an open end 114 and a proximal end 112 in a non-deployed configuration.

In block 604, the method can include affixing the proximal end 112 to a push wire 160 via a detachment feature 164.

In block 606, the method can include positioning a sleeve over the push wire 160 and the detachment feature 164 to prevent detachment of the proximal end 112 from the distal end of the push wire 160.

In block 609, the method can include delivering the expandable segment 110, push wire 160, and sleeve 170 to a treatment site via a microcatheter 600.

In block 610, the sleeve 170 can be slid proximally, thereby releasing the proximal end 112 of the segment 110 from the distal end of the push wire 160. In response, the segment 110 can expand to occlude the spherical cavity 10.

The tubular braid 110 of the example implant 100 can include memory shape material that can be heat set to a predetermined shape, can be deformed for delivery through a catheter, and can self-expand to an implanted shape that is based on the predetermined shape and confined by the anatomy of the aneurysm in which it is implanted.

The example implant 100 described herein can rely on a radial outward force to anchor the implant within the sac of an aneurysm. To this end, the braid 110 can be shaped to a predetermined shape having a diameter that is greater than its height so that the braid is radially constricted when implanted in an aneurysm. The ratio of diameter to height of the braid 110 in a respective predetermined shape can be within the range of 2:1 to 1:3 to treat aneurysms of many known sizes and shapes.

The descriptions contained herein are examples of embodiments of the invention and are not intended in any way to limit the scope of the invention. As described herein, the invention contemplates many variations and modifications of the implant, including alternative materials, alternative geometries, alternative detachment features, alternative delivery systems, alternative means for forming a braid into a predetermined shape, alternative treatment methods, etc. These modifications would be apparent to those having ordinary skill in the art to which this invention relates and are intended to be within the scope of the claims which follow.

What is claimed is:

1. An endovascular implantation system, comprising:
    an occlusive segment configured to occlude a spherical cavity and comprising an open end and a proximal end;
    a push wire positioned proximal of the proximal end of the occlusive segment and comprising one or more indentations on an outer surface of the push wire approximate a distal end of the push wire;

a detachment feature affixed to the proximal end of the occlusive segment and shaped to at least partially recess into the one or more indentations of the push wire; and a sleeve surrounding at least a portion of the push wire, wherein in a non-deployed configuration, the sleeve surrounds at least a portion of the detachment feature and thereby prevents release of the proximal end of the occlusive segment from the push wire, and wherein in a deployed configuration, the sleeve is retracted proximally from the detachment feature to thereby detach the occlusive segment from the push wire.

2. The endovascular implantation system of claim 1, wherein the detachment feature further comprises a plurality of wire loops extending from the proximal end of the occlusive segment that are at least partially recessed into the one or more indentations of the push wire in the non-deployed configuration.

3. The endovascular implantation system of claim 2, wherein the one or more indentations comprise a plurality of laser-etched pockets, each of the laser-etched pockets shaped to receive a corresponding wire loop of the plurality of wire loops.

4. The endovascular implantation system of claim 1, wherein the detachment feature further comprises a plurality of balls extending from the proximal end that are configured to fit into the one or more indentations of the push wire in the non-deployed configuration.

5. The endovascular implantation system of claim 1, wherein in the deployed configuration, the occlusive segment expands to occlude the spherical cavity.

6. The endovascular implantation system of claim 1, wherein in the deployed configuration the occlusive segment extends in a distal direction from the proximal end and comprises two inversions separating three sections which at least partially overlap each other such that the proximal end is affixed to an innermost section of the three sections, and a middle section of the three sections extends between the two inversions and is positioned within an outermost section and around the innermost section.

7. The endovascular implantation system of claim 1, further comprising:

a microcatheter configured to deliver the occlusive segment, the push wire, and the sleeve to the spherical cavity in the non-deployed configuration, the microcatheter comprising a lumen, wherein the segment comprises a diameter in the non-deployed configuration sized to fit within the lumen of the microcatheter.

8. The endovascular implantation system of claim 1, further comprising a band approximate the proximal end of the occlusive segment, wherein the band comprises radiopaque material.

9. The endovascular implantation system of claim 8, wherein, in the deployed configuration, the open end is positioned approximate a distal wall of the spherical cavity, and the band is suspended within the spherical cavity.

10. A method for constructing an endovascular implantation system, the method comprising:

providing an occlusive segment comprising an open end and a proximal end;

shaping, as follows, the occlusive segment to a predetermined shape to which the segment is capable of self-expanding:

inverting the segment to form a proximal inversion folded toward a distal direction thereby defining an outermost section of the segment, and inverting the segment to form a distal inversion folded toward the proximal direction thereby defining a middle section between the proximal and distal inversion of the segment that is at least partially surrounded by the outermost section and defining an innermost section between the distal inversion and the proximal end that is at least partially surrounded by the middle section;

providing a detachment feature affixed to the proximal end of the segment;

providing a push wire comprising one or more indentations approximate a distal end of the push wire;

recessing at least a portion of the detachment feature into the one or more indentations of the push wire; and positioning a sleeve to at least partially surround the distal end of the push wire and the detachment feature.

11. The method of claim 10, wherein the sleeve is effective to retain the proximal end of the occlusive segment attached to the push wire.

12. The method of claim 10, wherein the detachment feature further comprises a plurality of wire loops extending from the proximal end that are configured to fit into the one or more indentations positioned on the distal end of the push wire.

13. The method of claim 12, wherein the one or more indentations comprise a plurality of laser-etched pockets, each of the laser-etched pockets shaped to fit a corresponding wire loop of the plurality of wire loops.

14. The method of claim 10, wherein the detachment feature further comprises a plurality of balls extending from the proximal end that are configured to fit into the one or more indentations positioned on the distal end of the push wire.

15. A method of occluding a spherical cavity, the method comprising:

providing an expandable segment comprising an open end and a proximal end in a non-deployed configuration;

affixing the proximal end to a push wire via a detachment feature;

positioning a sleeve over the push wire and the detachment feature to prevent detachment of the proximal end from a distal end of the push wire;

delivering the expandable segment, push wire, and sleeve to a treatment site via a microcatheter; and sliding the sleeve proximally, thereby releasing the proximal end from the distal end of the push wire and causing the expandable segment to expand to a deployed configuration to occlude the spherical cavity.

16. The method of claim 15, wherein the detachment feature further comprises a plurality of wire loops extending from the proximal end that are configured to fit into one or more indentations positioned on a distal end of the push wire.

17. The method of claim 16, wherein the one or more indentations comprise a plurality of laser-etched pockets, each of the laser-etched pockets shaped to fit a corresponding wire loop of the plurality of wire loops.

18. The method of claim 15, wherein the detachment feature further comprises a plurality of balls extending from the proximal end that are configured to fit into the one or more indentations positioned on the distal end of the push wire.

19. The method of claim 15, wherein in the deployed configuration, the proximal end of the expandable segment is flush with a proximal end of the spherical cavity.

20. The method of claim 19, wherein in the deployed configuration the expandable segment comprises two inversions separating three sections which at least partially overlap each other such that the proximal end of the expandable segment is affixed to an innermost section of the three sections and a middle section of the three sections extends between the two inversions and is positioned within an outermost section and around the innermost section.

* * * * *